United States Patent [19]
Heller et al.

[11] Patent Number: 5,792,342
[45] Date of Patent: Aug. 11, 1998

[54] APPARATUS FOR COORDINATING CHEMICAL TREATMENT OF SEWAGE

[75] Inventors: Jon D. Heller, Denver; Kenneth J. Heller, Englewood; Timothy Reeves, Arvada, all of Colo.

[73] Assignee: NuTech Environmental Corporation, Denver, Colo.

[21] Appl. No.: 606,636

[22] Filed: Feb. 26, 1996

Related U.S. Application Data

[63] Continuation of Ser. No. 242,132, May 13, 1994, abandoned, which is a continuation-in-part of Ser. No. 947,301, Sep. 18, 1992, Pat. No. 5,312,594.

[51] Int. Cl.$^6$ .................................................. B01D 17/12
[52] U.S. Cl. .......................... 210/96.1; 137/3; 137/88; 210/101; 210/140; 210/198.1; 210/916; 210/921; 364/510; 366/152.1; 422/116
[58] Field of Search ........................ 210/140, 139, 210/170, 201, 202, 205, 713, 744, 752, 96.1, 101, 134, 137, 143, 199, 747, 916, 919–921, 87, 198.1; 422/106, 111, 116; 364/502, 510; 137/3, 4, 88, 93, 98; 366/152.1

[56] References Cited

U.S. PATENT DOCUMENTS

| | | | |
|---|---|---|---|
| 2,243,826 | 5/1941 | Nielsen et al. | 210/921 |
| 2,640,807 | 6/1953 | Rice | 210/919 |
| 3,730,884 | 5/1973 | Burns et al. | 210/170 |
| 3,853,764 | 12/1974 | Armstrong | 210/195 |
| 3,920,550 | 11/1975 | Farrell, Jr. et al. | 210/86 |
| 4,465,593 | 8/1984 | Wemhoff | 210/96.1 |
| 4,618,421 | 10/1986 | Kantor | 210/919 |
| 4,804,478 | 2/1989 | Tamir | 210/752 |
| 4,830,757 | 5/1989 | Lynch et al. | 210/742 |
| 4,882,069 | 11/1989 | Pohoreski | 210/713 |
| 5,013,442 | 5/1991 | Davis et al. | 210/96.1 |
| 5,114,586 | 5/1992 | Humphrey | 210/919 |
| 5,356,458 | 10/1994 | Javadi et al. | 210/916 |
| 5,614,102 | 3/1997 | Sakurada | 210/919 |
| 5,618,440 | 4/1997 | Mason | 210/198.1 |

*Primary Examiner*—Joseph W. Drodge
*Attorney, Agent, or Firm*—Holme Roberts & Owen

[57] ABSTRACT

A method and apparatus for treating nuisance odor streams is provided. One embodiment of the invention is directed to a method and apparatus in which deodorizing chemical agents are applied to an evaporative reaction pack situated within a gas chamber having an air stream running therethrough. The evaporative reaction pack provides a reaction zone within which the chemical agent is evaporated to facilitate a gas-gas or vapor phase interaction between the chemical agent and odoriferous compounds contained in the air stream. Another aspect of the present invention relates to a method and apparatus for batch processing of sewage treatment agents within a wet well to prevent the formation of undesired compounds. In one embodiment, a predetermined amount of chemical agent, sufficient for treating the amount of sewage that the well can hold, is added to an evacuated wet well in coordination with the pumping of sewage from the wet well. Yet a further aspect of the invention relates to a method and apparatus for coordinating the automatic dispensing of sewage treatment chemicals at several locations in a sewage collection system to make efficient and effective use of the treatment chemicals and reduce or eliminate manual application of such chemicals.

25 Claims, 12 Drawing Sheets

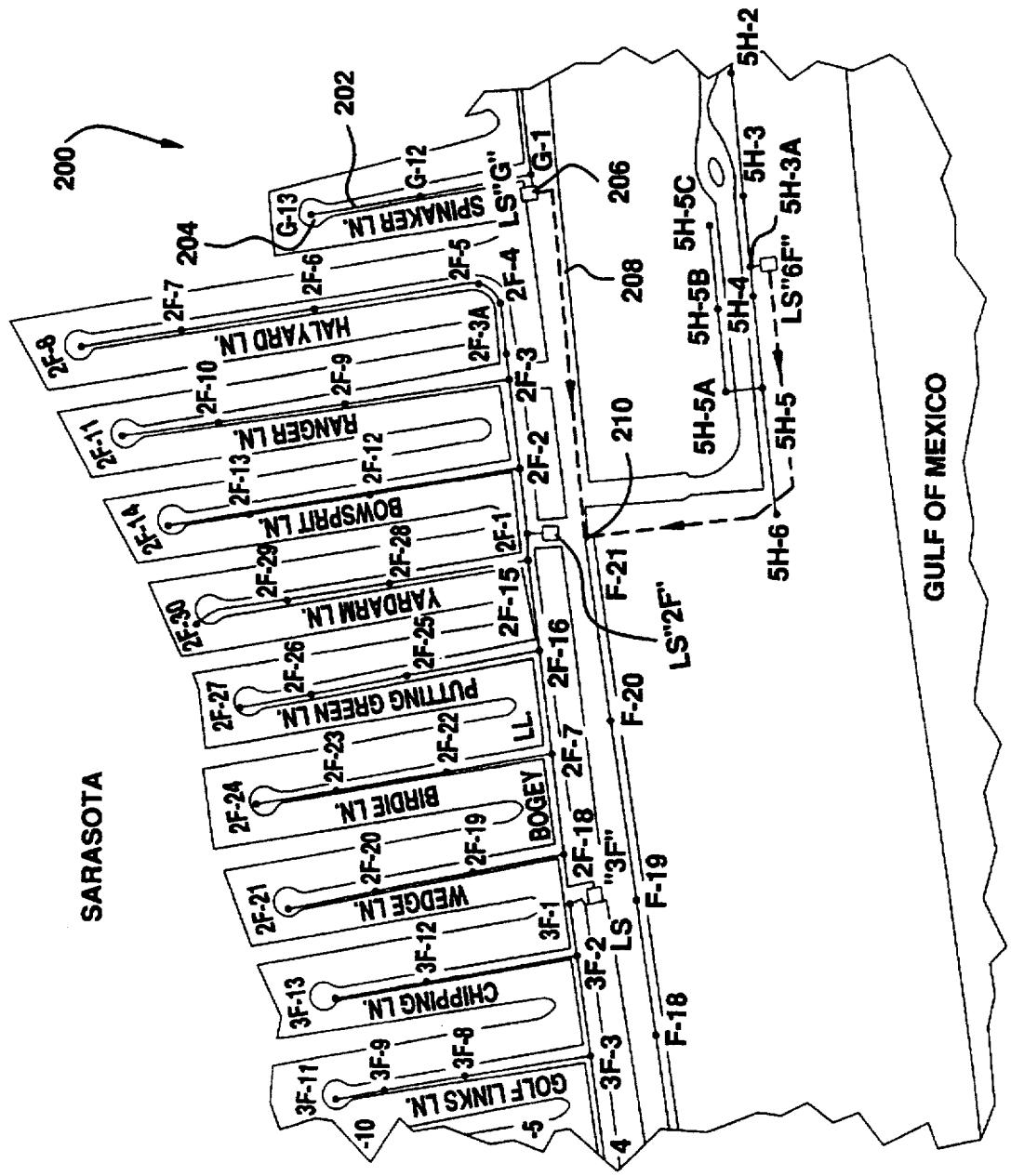

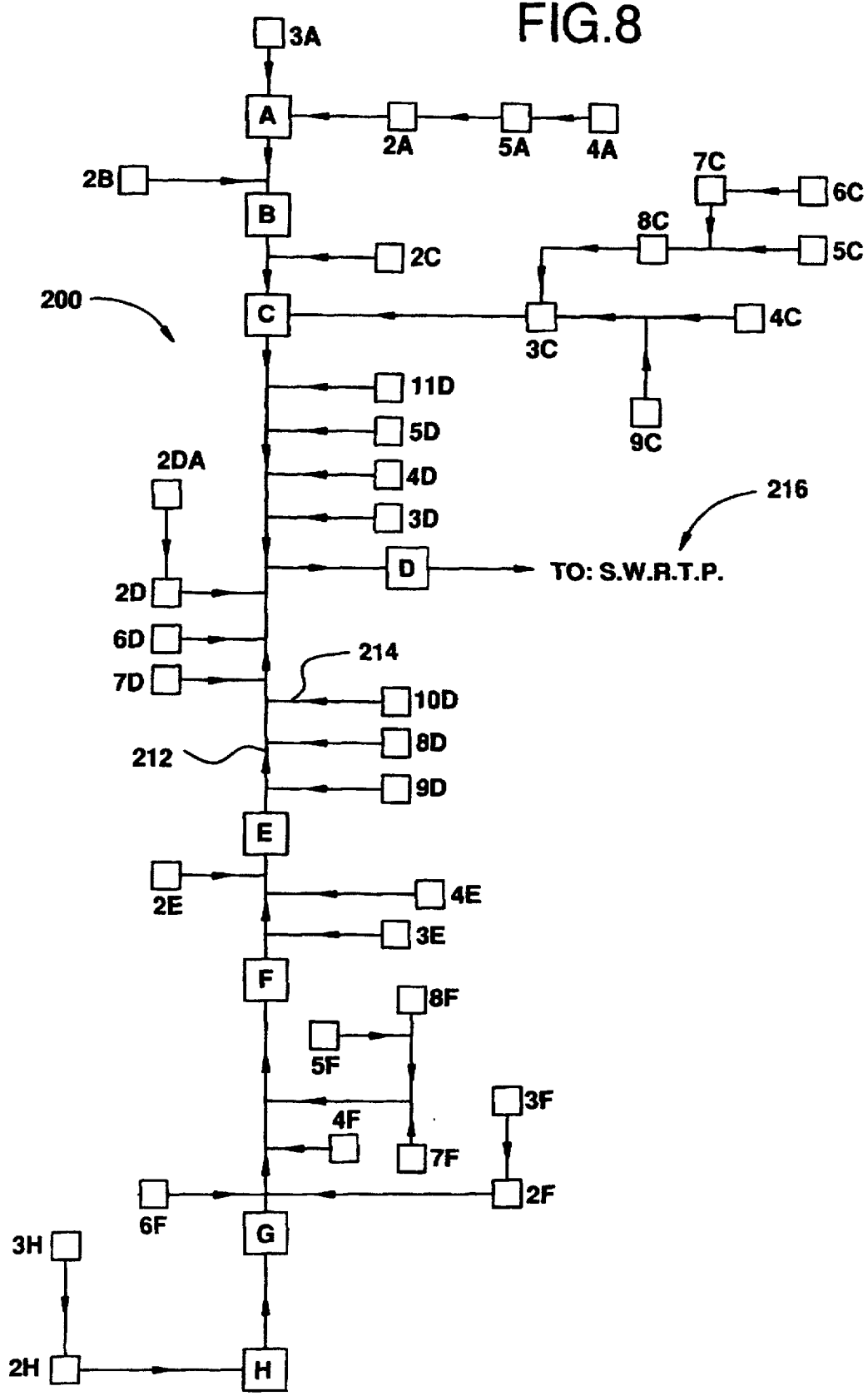

APPARATUS FOR COORDINATING CHEMICAL TREATMENT OF SEWAGE

CROSS REFERENCE TO RELATED APPLICATION

The present application is a continuation of U.S. patent application Ser. No. 08/242,132, filed May 13, 1994 now abandoned, which is a continuation-in-part application of U.S. patent application Ser. No. 07/947,301, filed Sep. 18, 1992 now U.S. Pat. No. 5,312,594.

FIELD OF THE INVENTION

The present invention relates generally to a method and apparatus for removing undesirable odorous compounds from air or gas streams and more particularly to a method and apparatus for reacting odoriferous compounds with vaporous deodorizing compounds within a reaction zone to remove odorous components from the air or gas stream. Another aspect of the present invention relates to a method and apparatus for conditioning sewage within a wet well to prevent the formation of undesired odorous compounds. Yet a further aspect of the present invention relates to the treatment of a sewage collection system by the coordinated dispensing of sewage treatment chemicals at two or more points in the system.

BACKGROUND OF THE INVENTION

The general objective in the treatment of gas streams from industrial and sewage plants is to combine, counteract, react and/or remove from such gas streams odorous constituents, such as volatile organic compounds (VOCs) and volatile inorganic compounds (VICs). It is well known in the prior art to remove odors from waste gases in liquid-gas reactions through absorption utilizing spray mist scrubber systems and packed bed scrubber systems. In conventional mist scrubber systems, an aqueous solution containing one or more chemicals reactive toward one or more of the odorous contaminants (typically an oxidizing compound and a hydroxide compound used for pH modification) is atomized to create liquid droplets which are dispersed into an odorous gas stream. The finely atomized liquid droplets absorb the malodorous compounds and allow oxidation of such odors, which removes them from the gas stream. The reaction vessels are constructed to provide desired absorption/reaction times for the odorous gas and the atomized aqueous/chemical fog, such absorption/reaction times typically range from about 5 to about 30 seconds or more for mist systems, and approximately 2 seconds for packed bed scrubbers.

These and other traditional approaches have in common either a relatively long contact time between the odorous gas and the treating liquid, in mist scrubbers, or for packed bed scrubbers, they use a relatively large volume of liquid per volume of gas treated. Conventional mist and packed bed scrubber systems can be inefficient with respect to the amount of chemical used. Moreover, these conventional systems tend to be large and are expensive to construct and operate.

In other conventional liquid-gas absorption processes, packed bed scrubber systems are utilized to provide large surface areas for the liquid-gas reaction to occur. However, packings used in packed bed scrubbers are often clogged by hard water, solid particulates and reaction by-products, negatively affecting the efficiency and overall function of such packed bed scrubber systems. Moreover, the size and expense of packed bed scrubber systems often preclude their use in many applications.

Problems in the treatment of sewage have also been encountered in the storage of sewage for extended periods of time. Among the problems, facultative bacteria present in sewage can react with sulfates in the absence of oxygen, thereby producing hydrogen sulfide, a malodorous poisonous gas, as well as other undesired odorous compounds. A combination of hydrogen sulfide gas with water vapor forms sulfuric acid, which causes deterioration of sewer pipes and sewer systems. Other undesirable compounds and gases may also form and need to be treated.

In conventional sewage systems, sewage is often held in various process apparatuses, such as a wet well, prior to treatment. Methods have been previously employed whereby chemicals are continuously fed into the wet well pump discharge line when the pump is operating or fed continually into the wet well. A continuous release system, however, may involve the undertreatment or overtreatment of sewage depending upon the time required for the wet well to fill to a predetermined level prior to evacuation. Alternatively, other systems treat malodorous sewage during the transport of such fluid from the wet well to other treatment containers. However, the sewage in the wet well prior to evacuation has the opportunity to ferment bacteria that produce undesirable, odoriferous compounds.

Another area of concern is the manner in which the sewage collection system, i.e., the collection of lines that convey sewage to a sewage treatment plant, is treated to inhibit the formation of undesirable chemicals or neutralize undesirable chemicals that have already formed. One presently known method for treating a sewage collection system is to manually dispense a sewage treatment chemical at various locations in the system. This method is typically labor intensive and generally makes relatively inefficient and sometime ineffective use of the sewage treatment chemical. Another known method of treating a collection system involves the use of a plurality of independent dispensers dispersed throughout the system with each dispenser continuously dispensing a sewage treatment chemical into the system. These systems also tend to make relatively inefficient and many times ineffective use of the sewage treatment chemical. Consequently, there is a need for a method and/or apparatus for chemically treating a sewage collection system that addresses the deficiencies of the known treatment systems.

SUMMARY OF THE INVENTION

One aspect of the present invention relates to a vapor phase deodorizing apparatus which effectively brings into contact an air or gas stream containing undesired odorous compounds with one or more volatile deodorizing compounds or chemical agents in a reaction zone so as to react the odorous compound with the deodorizing compound in an efficient gas-gas deodorizing reaction.

In one embodiment of the method invention, a volatile or vaporous deodorizing chemical is evaporated in a reaction zone through which a odoriferous containing air stream is passed through, thereby allowing a gas-gas reaction to occur. The vaporous deodorizing chemicals of the present invention can be any of a number of various odor counteractants and odor reactants. The deodorizing chemical is brought into contact with an evaporative reaction pack by means of one or more spray nozzles, such that spray droplets of deodorizing chemical are carried into the evaporative reaction pack by the air stream. The evaporative reaction pack into which the chemical spray is propelled and which simultaneously receives the malodorous air stream, is designed so as to facilitate the evaporation of the chemical agents and the reaction of the odorous compounds in the air or gas stream with the chemical agents. Liquid formed from the reacted malodorous compounds with deodorizing chemicals, as well as water accumulating within the evaporative reaction pack are removed from the reaction zone by gravity, forming drops of liquid which fall into the oncoming air stream and exit through a drain provided in the gas chamber.

An alternative embodiment of the invention utilizes a series of spray devices and evaporative reaction packs to, for example, treat the gas stream with several different chemicals.

Another embodiment employs an evaporative reaction pack downstream from the evaporative reaction pack or packs to remove moisture from the treated air stream.

Yet another embodiment of the apparatus employs two evaporative reaction packs, one oriented downstream, with respect to the gas flow, from the spray device and the other oriented upstream and with one oriented above the other, to promote efficient use of the chemical. Specifically, chemical that does not react in the upper evaporative reaction pack can, once the pack becomes saturated, precipitate down onto the lower evaporative reaction pack where it has another opportunity to react with the malodorous gas stream and in essence pre-treat the gas stream as the chemical is further expended, in some cases providing near 100% utilization of the chemical.

Another aspect of the present invention involves the batch treatment of sewage stored in sewage storage vessels, such as wet wells. In one embodiment of the invention, a predetermined amount of treatment chemical is added to a wet well, which directly receives raw sewage from, for example, one or more houses, after such wet well is evacuated or when such wet well contains sewage at some predetermined level. Untreated sewage enters the wet well and interacts with a predetermined amount of chemical until such wet well reaches a predetermined level. At such point, a pump is started which operates to evacuate the wet well to a force main or gravity main. When the wet well is sufficiently evacuated or at some predetermined level, the pump operation ceases, thereby allowing the wet well to refill with sewage. Upon the cessation of pumping and/or the substantial evacuation or attainment of a predetermined level in the wet well, a signal is conveyed to a chemical treatment reservoir to release another predetermined amount of treatment chemical sufficient to treat a predetermined volume of sewage in the wet well. As such, this embodiment of the present invention provides for an automatic, continuous batch feeding process and apparatus for treating sewage within a wet well or sewage storage vessel in a manner that provides for substantially equal treatment of all sewage passing through the wet well and prevents the formation of undesired odors or compounds without unduly wasting the treatment chemicals.

Yet a further aspect of the present invention involves the treatment of a sewage collection system to inhibit the formation of undesirable chemicals or substantially neutralize undesirable chemicals that have already formed in the system. In one embodiment of the invention, a first dispenser is located to inject a sewage treatment chemical into a first line of a collection system, a second dispenser is located to inject a sewage treatment chemical into a second line of a collection system whose sewage eventually commingles with the sewage of the first line and flows into a third line, and a device for automatically coordinating the dispensing of the sewage treatment chemicals so that the treatment chemicals from each of the first and second lines reach the third line at substantially the same time. As a consequence of this coordinated treatment of the sewage collection system, relatively efficient and effective use of the chemicals is obtained.

In one embodiment, the coordinating device includes a processor that, based upon information that has been provided to it, causes the dispensers to inject the sewage treatment chemicals at the appropriate times for achieving the treatment of downstream lines as previously mentioned. The processor can be provided with certain information, such as flow rates, via a user interface. Information can also be provided to the processor via sensors. For example, if the flow rates in the various lines into which chemicals are injected vary, flow rate sensors can be employed to provide the processor with flow rate related information. One or more chemical sensors can also be employed to monitor sewage related chemical parameters and provide this information to the processor. In operation, a chemical sensor may detect an undesirable condition of chemicals in the sewage and, in response, the processor would coordinate the injection of treatment chemicals into the sewage via the dispensers so that the treatment chemicals from two or more lines reach their confluences at substantially the same time and can be used to treat the downstream system.

In another embodiment, the coordinator is preprogrammed with information on the sewage collection system and causes the dispensers to inject their chemicals at predetermined times. For example, the coordinator may cause one dispenser to inject its chemical into a line every four weeks and another dispenser to inject its chemical into a line every three weeks. The coordinator, in this case, can be centrally located or separate timers can be associated with each dispenser.

BRIEF DESCRIPTION OF THE DRAWINGS

FIG. 8 is a schematic flow diagram of a typical sewage collection system for a medium size town.

DETAILED DESCRIPTION OF THE INVENTION

Figure 1:
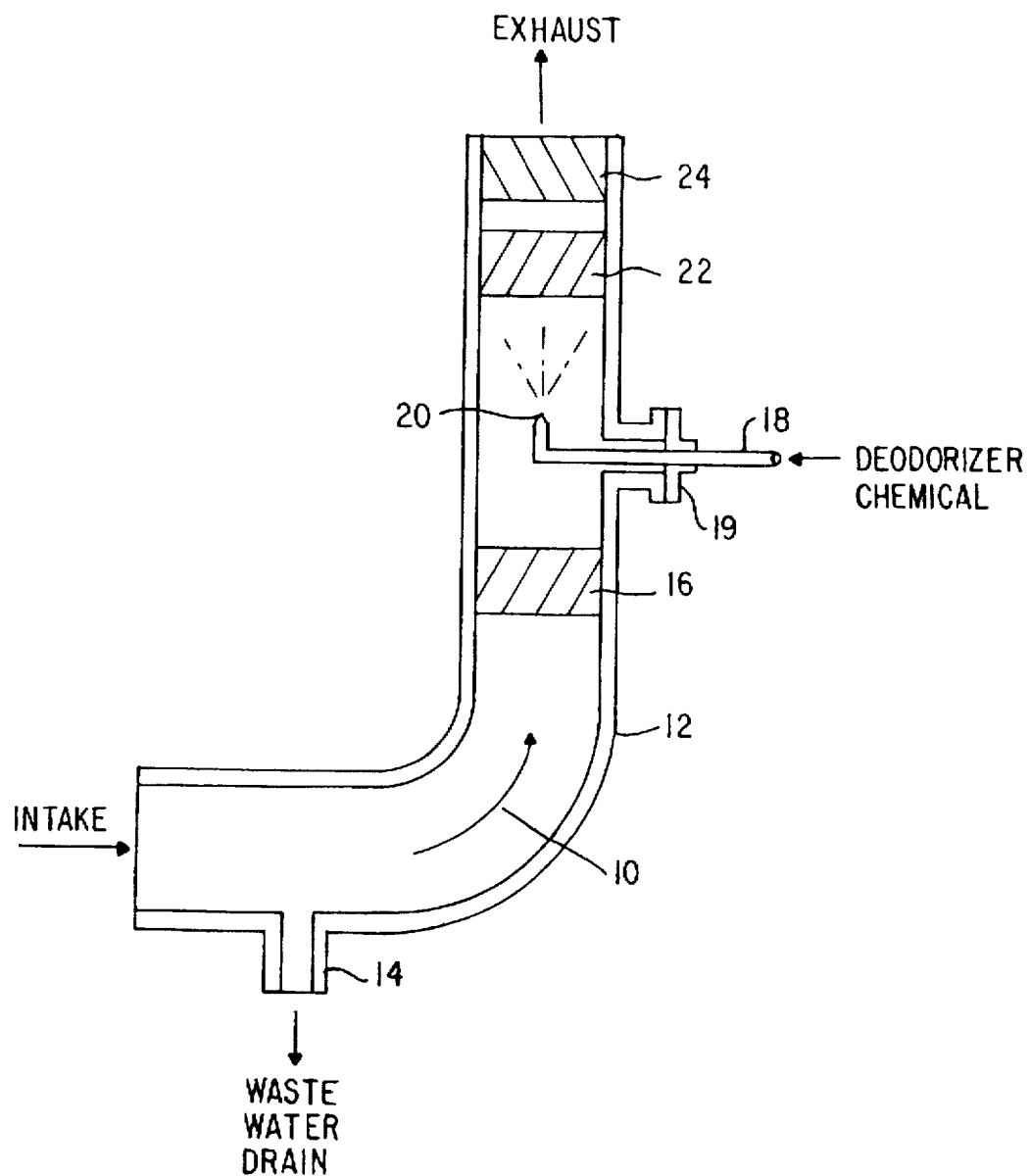
FIG. 1 is a schematic view of the deodorizing apparatus of the present invention.

The process and apparatus of the present invention may be understood by reference to the attached drawings. With respect to the apparatus shown in FIG. 1, an air or gas stream 10 containing odorous or otherwise undesirable constituents is passed into a gas chamber 12 and passes through a bottom evaporative reaction pack 16 for removing at least a portion of an odoriferous constituent, continues to travel upwards through a top evaporative reaction pack 22 for further removing the malodorous component of the gas stream and exits to the environment. The bottom evaporative reaction pact 16 also acts to equalize gas flow characteristics to facilitate uniform distribution of the fine droplets from the spray nozzle(s). A "chemical agent", which can be any volatile substance capable of reacting with undesired compounds, and specifically, with odorous compounds, is contacted with the air stream 10 in the bottom evaporative reaction pack 16, top evaporative reaction pack 22 and the volume therebetween such that gas-gas or vapor phase reactions occur between the chemical agent and the undesirable odorous compounds. Suitable chemical agents include odor counteractants such as those formulated from a blend of vegetable essential oils, and other reactants, such as NuTech's Chi-X Odor Eliminator, NuTralite Odor Eliminator, and DeAmine Odor Eliminator. The chemical agent can be carried in a dilutioning aqueous solution, and is present in the required concentration for the particular odor loading in the sewage, typically the concentration is about 0.3% to about 10%.

While the aqueous chemical agent can be contacted with the bottom and top evaporative reaction packs 16, 22 in any effective manner, in the illustrated embodiment it is applied to the evaporative reaction packs by using a spray means such as a nozzle 20. Additional nozzles can be employed if necessary for larger air flows. Thus, in one embodiment a nozzle 20, connected to a pressurized chemical spray supply line 18, is provided in the interior of the gas chamber 12. A desired amount of chemical agent mixed with water is delivered through the chemical supply line 18 and exists from the nozzle 20 to create an atomized fog or mist within the gas chamber 12.

An appropriate nozzle is selected and the pressure of the chemical spray is adjusted to coincide with the air stream flow 10 so that the desired amount of chemical agent is carried by the air stream into contact with the top evaporative reaction pack 22. Typically, the top evaporative reaction pack 22 becomes saturated with the chemical agent and, in many situations, more agent is present than capable of reacting with the malodorous agent in the gas stream 10 in the top evaporative reaction pack 22. In this case, the unused chemical agent precipitates, along with the reacted chemical agent, and falls to the bottom evaporative reaction pack 16 where it can now react with the gas stream 10 and, in effect, act as a pre-treatment of the gas stream 10 that promotes efficient utilization of the chemical agent.

The nozzle 20 used to apply the spray in the illustrated embodiment of the present invention preferably generates droplets of less than 200 microns, more preferably between 20 and 100 microns and most preferably between 50 and 60 microns. The nozzle 20 can be modified dependent upon the volume of the airstream 10 being treated. For example, the preferred nozzle 20, which is designed for use in a system treating a 1000 cfm air stream and handle approximately 0.6 gallons of the diluted chemical agent per hour, can be modified for different amounts of air flow and/or to distribute different amounts of the diluted chemical. Preferably, the nozzle 20 is positioned with a specially designed bracket/flange assembly 19 so that the nozzle 20 is easily removed from the gas chamber 12 for cleaning and maintenance.

While the orientation of the nozzle 20 shown in FIGS. 1 and 2 is in the direction of the air stream 10, it is also within the scope of the present invention to have the nozzle 20 spraying in a direction counter to the air stream 10. It is, however, of primary importance that the chemical agent is sufficiently and effectively applied to at least one of the bottom and top evaporative reaction packs 16, 22 in a manner so as to facilitate the desired evaporation and gas-gas reaction of chemical agent with the odorous air stream. The spray pattern produced by the nozzle 20 should encompass the area of the gas chamber and evenly contact the bottom surface of the top evaporative reaction pack 22.

A fan (not shown) can be provided in communication with the gas chamber to increase the velocity of the air stream 10 to facilitate the carrying of chemical agent onto the top evaporative reaction pack 22 if needed.

The application of the sprayed chemical agent onto the bottom and top evaporative reaction packs 16, 22 creates a film on the surfaces within the evaporative reaction packs 16, 22. The numerous convoluted surfaces within the bottom and top evaporative reaction packs 16, 22 afford effective evaporative surfaces for the chemical agent that enhance the chemical reaction between the air stream 10 and the chemical agent. Odor components within the air stream 10 enter the bottom and top evaporative reaction packs 16, 22 and react with the evaporated chemical agents, thus generating a liquid which accumulates on the surfaces of the evaporative reaction packs 16, 22, precipitates or condenses, and eventually falls to the bottom of the vessel 12 where it leaves the vessel via drain 14.

In the illustrated embodiment of the invention a bottom evaporative reaction pack 16 is provided which acts to redistribute unreacted chemical agent that falls from the top evaporative reaction pack 22. The accumulation of such liquid eventually coats the surfaces of the bottom evaporative reaction pack 16 with the chemical agent. The presence of unreacted chemical agents in the bottom evaporative reaction pack 16 allows for the interaction of odoriferous compounds in the air stream 10 entering the bottom evaporative reaction pack 16 and, in effect, pre-treats the gas stream 10 while, in many cases, substantially consuming the remaining chemical agent.

As described in greater detail below, the bottom and top evaporative reaction packs 16, 22 and the volume in between the packs provides a reaction zone where the incoming air stream 10 can react with the chemical agent. The convoluted construction of the bottom and top evaporative reaction packs 16, 22 facilitate the evaporation of chemical agent into a gas or vapor form to enable its reaction with odorous compounds in the air stream.

The top and bottom evaporative reaction packs 22, 16 are sometimes of identical construction. In general, the evaporative reaction packs 22, 16 are positioned so as to completely extend across the area of the gas chamber 12 and are of a sufficient thickness (depth) to accommodate a particular range of air stream 10 flows. For example, each of the evaporative reaction packs 16, 22 can have a depth of approximately four inches, which is sufficient to accommodate air stream 10 velocities of between 500 and 1100 feet per minute. Further, each of the evaporative reaction packs 16, 22 is preferably selected to be of sufficient depth to avoid, for a given air stream flow, an excessive pressure drop through the pack. The evaporative reaction packs 16, 22 depths are therefore selected in order to accomplish the evaporation of chemical agents for reaction with the malodorous component of the air stream and the condensation of substantially all other liquid components in the air stream 10 so that no substantial amount of liquid exits the pack with the exiting air stream 10. If, however, an undesirable amount of liquid is present in the exiting air stream, a demister 24 can be placed downstream relative to the direction of air flow to facilitate the condensation of such liquids.

A suitable evaporative reaction pack provides a chamber for facilitating or enhancing reaction between the chemical agent and the gas stream 10 by promoting evaporation of chemical agents so that the desired gas-gas or vapor phase reaction can occur between the chemical agent and the air stream. The evaporative reaction packs 16, 22 each essentially form a reaction zone in which evaporation of the chemical agent is facilitated and reaction between the gaseous chemical agent can then occur with odoriferous compounds contained in the air stream 10. Specifically, the preferred packs 16, 22 promote substantially even distribution of air, as well as deodorizing chemical carried therein, over substantially the entire surface area of the packs. As a result, atomized droplets of aqueous chemical agents carried in the air stream 10 are substantially evenly distributed over the surfaces within the evaporative reaction pack 22.

The evaporative reaction pack is preferably constructed to permit the multiple channeling of the incoming air stream 10 through the reaction zone with little loss of air pressure, while simultaneously facilitating the contact of incoming air with numerous other channeled air streams within the reaction zone. Within the reaction zone, air streams are directed so as to collide with other air streams, providing circulating eddies of air currents and other accelerated air currents within the reaction zone. The air channel intersections create miniature centrifugal separators or vortices that variably accelerate and decelerate the air stream passing through the reaction zone. Such air movement through the reaction zone facilitates the evaporation of chemical agent from the aqueous solution and thereby allows a gas-gas or vapor phase reaction to occur between the odoriferous compounds in the air stream and the chemical agent. Alternate air channels are therefore provided with different angles throughout the reaction zone to create vortices and intersections which facilitate the forced mingling of odorous components in the air stream 10, and chemical deodorizing agents from the liquid spray, as the air stream 10 passes through the evaporative reaction pack 16, 22.

Figure 2A:
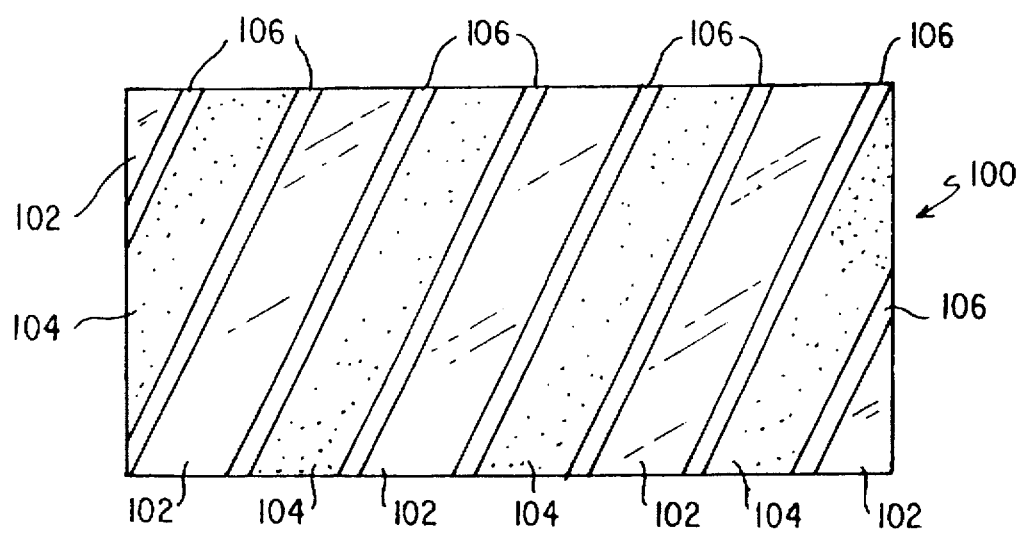
FIG. 2A is a side view of the evaporative reaction pack used in the present invention.
Figure 2B:
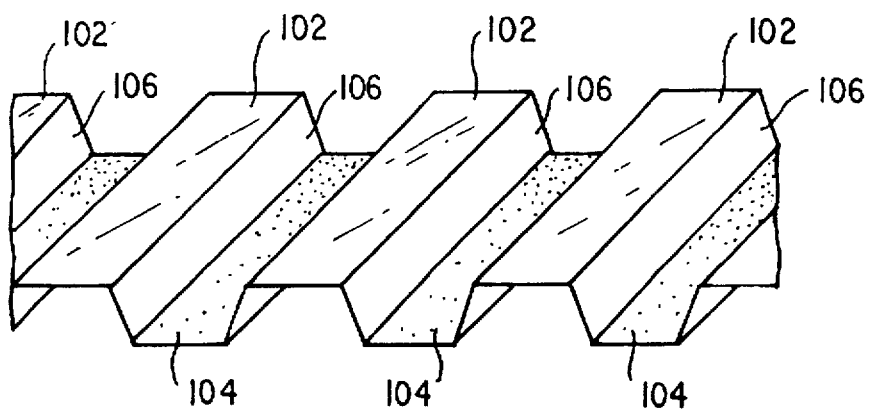
FIG. 2B is a perspective view of one layer of the evaporative reaction pack used in the present invention.
Figure 3:
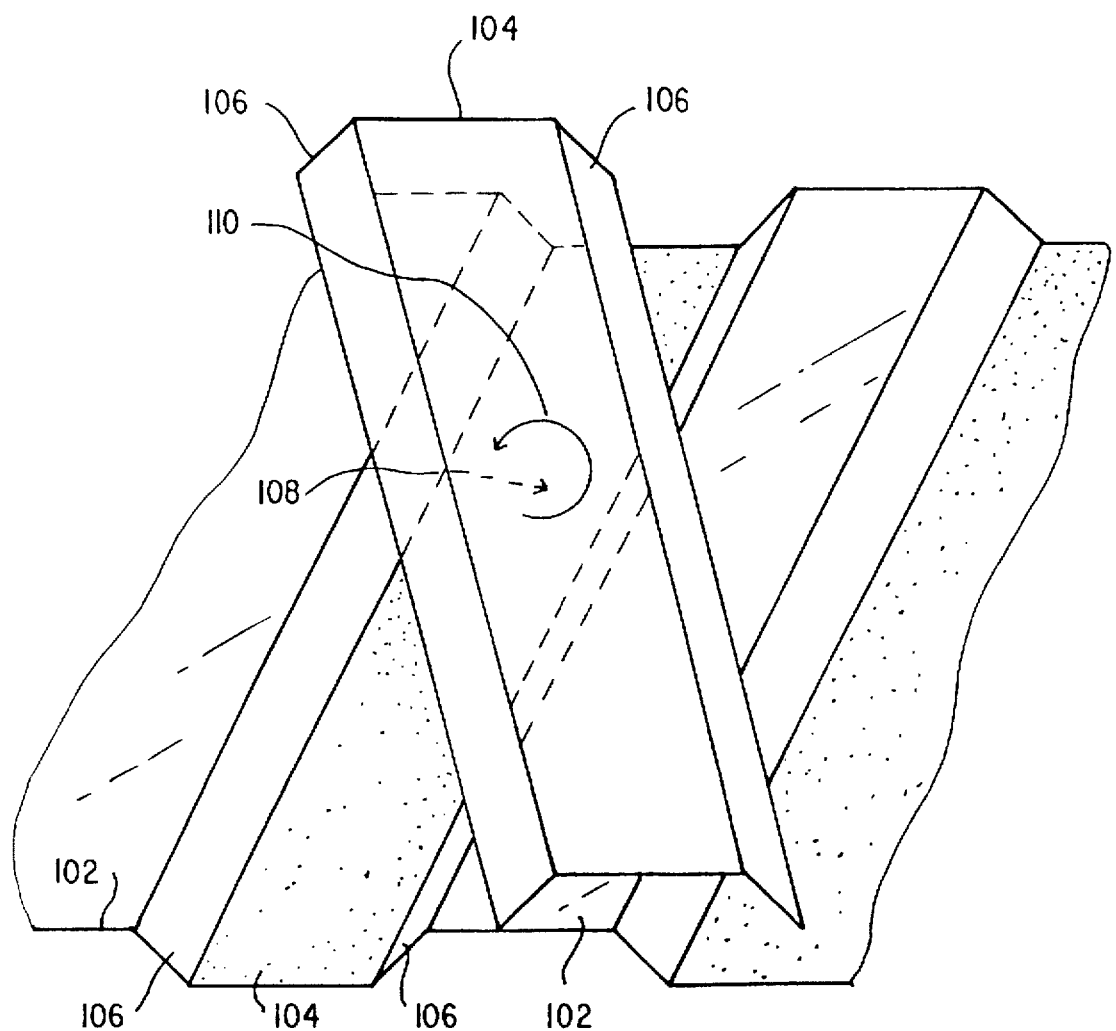
FIG. 3 is a perspective view of the two layers evaporative reaction pack that illustrates the vortex producing intersection of the channels associated with the two layers.
Figure 4:
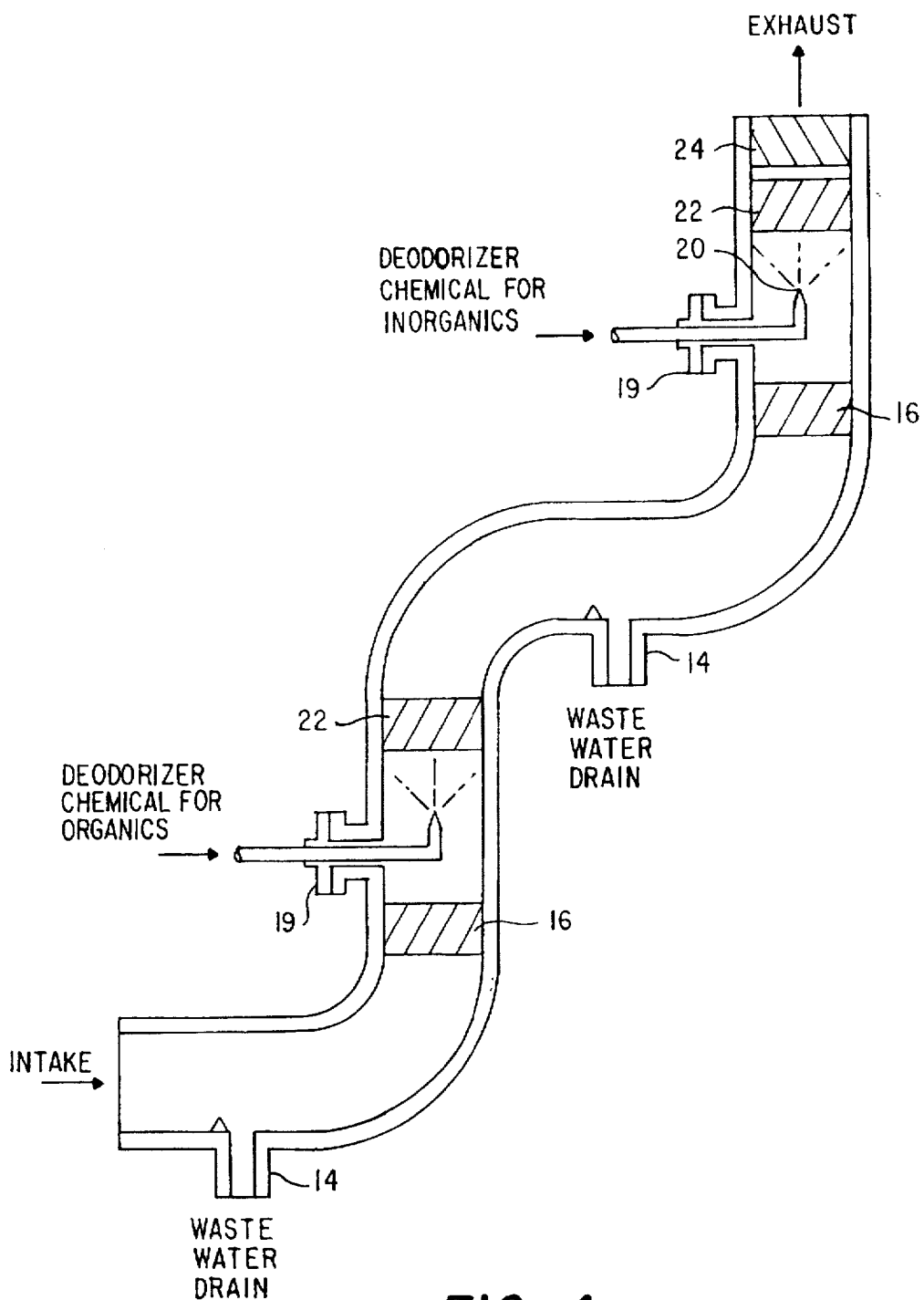
FIG. 4 is a schematic view of the present invention showing the ability to connect individual apparatuses in series to accommodate different or supplemental deodorizing treatments.

A suitable evaporative reaction pack can be obtained from Brentwood Industries, located in Reading, Pa., such evaporative reaction pack having a three-eights inch convoluted cross-flow packing structure that is illustrated in FIGS. 2A, 2B, and 3. A single layer 100 of the evaporative reaction pack is illustrated in FIGS. 2A and 2B. The layer 100 includes mesas 102 that are separated from channels 104 by sloping side members 106. The mesas 102, channels 104, and sloping side members 106 all run at an angle of approximately 60° relative to a plane perpendicular to the direction of the airstream flow. As illustrated in FIG. 3, an evaporative reaction pack is realized by juxtaposing two or more of the layers 100 such that the channels 104 of adjacent layers cross or intersect at point 108. The intersecting channels, it was discovered, produced vortices 110, when an air or gas stream is passed through the pack. As a result, when the air stream 10 which is carrying the chemical agent enters a pack, the resulting vortices created by the pack distribute the chemical agent over the surfaces of the pack for evaporation and promote the reaction between the gas and the evaporated chemical agent by forcing them into intimate contact with one another.

In a preferred embodiment, the evaporative reaction pack 16, 22 is designed in a convoluted structure having numerous vortices therein so that the air stream 10 entering the evaporative reaction pack 16, 22 is channelled and alternately accelerated and decelerated around and between sharply converging surfaces within the evaporative reaction pack. The design of the evaporative reaction pack 16, 22 thus facilitates the mixing of air from various channels within the evaporative reaction pack 16, 22, achieving an even distribution of air through the evaporative reaction pack 16, 22 significant mixing of the air stream 10 within the reaction zone, and substantial surface contact of the air stream 10 within the evaporative reaction pack.

The evaporative reaction packs 16, 22 of the present invention do not significantly create a high pressure drop in the gas chamber. In one embodiment, the pressure drop through a four inch evaporative reaction pack is only about one-quarter to three-eights of an inch of water column. As a result, the apparatus can be operated in a cost-effective manner because little energy needs to be expended in overcoming the apparatus's resistance to air flow. Stated another way, the apparatus exhibits little resistance to air flow, and is therefor energy efficient.

A preferred pack will allow a particular air flow channel in such evaporative reaction pack 16, 22 to cross with other air flow channels about five to eight times in a depth of about four inches.

In a preferred embodiment of the invention, the detention time of chemical agents and odoriferous compounds within the air stream is approximately one third of a second, compared with two to over thirty seconds of detention time in conventional mist tower and packed tower devices.

The air stream passing through the reaction zone should be of sufficient velocity to carry the chemical deodorizing agent into, but not completely through, the evaporative reaction pack to effect desired evaporation of chemical agents. Upon evaporation, the deodorizing chemical vapor is able to react with malodorous compounds and to coalesce on the surface of the evaporative reaction pack, ultimately forming drops that fall from the reaction zone through a drain or air inlet at a lower portion of the apparatus. To promote efficient utilization of the chemical agent, a series of fixed media evaporative reaction packs can be situated in the contact gas chamber.

Depending upon the volume of air stream 10 to be treated and the intensity of odors encountered, a suitable evaporative reaction pack 16, 22 is selected of appropriate depth and size to facilitate the effective evaporation of chemical agent and reaction with odorous compounds in such air stream 10. In one embodiment, the evaporative reaction pack 16, 22 preferably has sufficient cross-sectional area and depth sufficient to treat both low and high odor intensity air streams 10 having volumes of up to 15,000 cubic feet per minute.

In one embodiment, the evaporative reaction pack 22 is positioned within the gas chamber 12 a sufficient distance from the spray nozzle 20 so as to enhance a substantially even distribution of the liquid spray across the extent of the evaporative reaction pack 22 structure. The efficiency of the apparatus depends, to some extent, on a balance of air stream 10 velocities, spray nozzle 20 droplet size and spray application, together with the configuration and proximity of the evaporative reaction pack 16, 22. For example, if the volume of air within a gas chamber is too great, or alternatively if the depth of the evaporative reaction pack 16, 22 is too small, then an insufficient reaction zone will be created and liquid containing chemical agent therein may be transported through the evaporative reaction pack 22 with the air stream 10 without achieving desired evaporation and reaction with odor compounds.

In one embodiment of the present invention, approximately one gallon of water and deodorizing chemical mixture per hour is utilized. This is more efficient than known conventional liquid-gas devices that typically utilize from sixty to over six hundred gallons per hour of liquid to treat similar volumes of air. The superior efficiency of the present invention is believed to be principally due to the improved and faster vapor phase reaction of malodorous compounds with gaseous deodorizing chemical agents achieved by the apparatus.

While only one nozzle 20 is shown in FIG. 1, it is to be understood that a plurality of such nozzles 20 can be employed depending upon the volume of air stream 10 to be treated and nozzle spray pattern requirements. Moreover, arrangement of more than one apparatus of the present invention within an air stream, as shown in FIG. 2, can be employed to treat various types of odoriferous components contained such air stream 10. For instance, a gas chamber 12 may be fitted with several stages of evaporative reaction packs 16, 22 and nozzles 20, each nozzle 20 capable of providing a distinct chemical reactant spray. Such an arrangement therefore allows for the treatment of an air stream 10 having multiple contaminants therein.

In comparison with conventional liquid-gas treatment devices, the present invention provides for a compact, relatively inexpensive unit to make and operate that is able to effectively remove odorous compounds from air streams 10. Traditional packed tower devices, for treating 1000 cfm, for example, typically include scrubbers of eighteen to twenty-four inches in diameter and that are over twenty feet in height, containing approximately ten feet of packing material. In comparison, the present invention can use a twelve inch diameter chamber and is generally less than six feet in height. The present system is therefore capable of being easily retrofitted in existing foul air ventilation systems. In comparison with packed tower structures, considerable cost savings are achieved due to the elimination of the costly packed media that do not redirect the air flow of the air stream in a manner so as to achieve the evaporative function facilitating the gas-gas reaction of the present invention.

The present invention has reduced the energy requirements over both conventional spray tower systems and packed tower systems. Spray tower systems, while having relatively low pressure drops (i.e., about ½ inch) require significant energy to power an air compressor required to generate the pressurized, atomized liquid sprays used in such systems. Packed towers typically have substantial pressure drops of up to three inches and therefore require significantly more energy to overcome these pressure drops. Moreover, in the present invention application of chemical agents to the air stream 10 can be performed without the use of compressed air since only pressure atomization of a chemical agent is required. Using the evaporative reaction pack entrainment system of the present invention, lower chemical costs are encountered due to the increased efficiency of the reaction of the chemical agent with the air stream 10.

Figure 5:
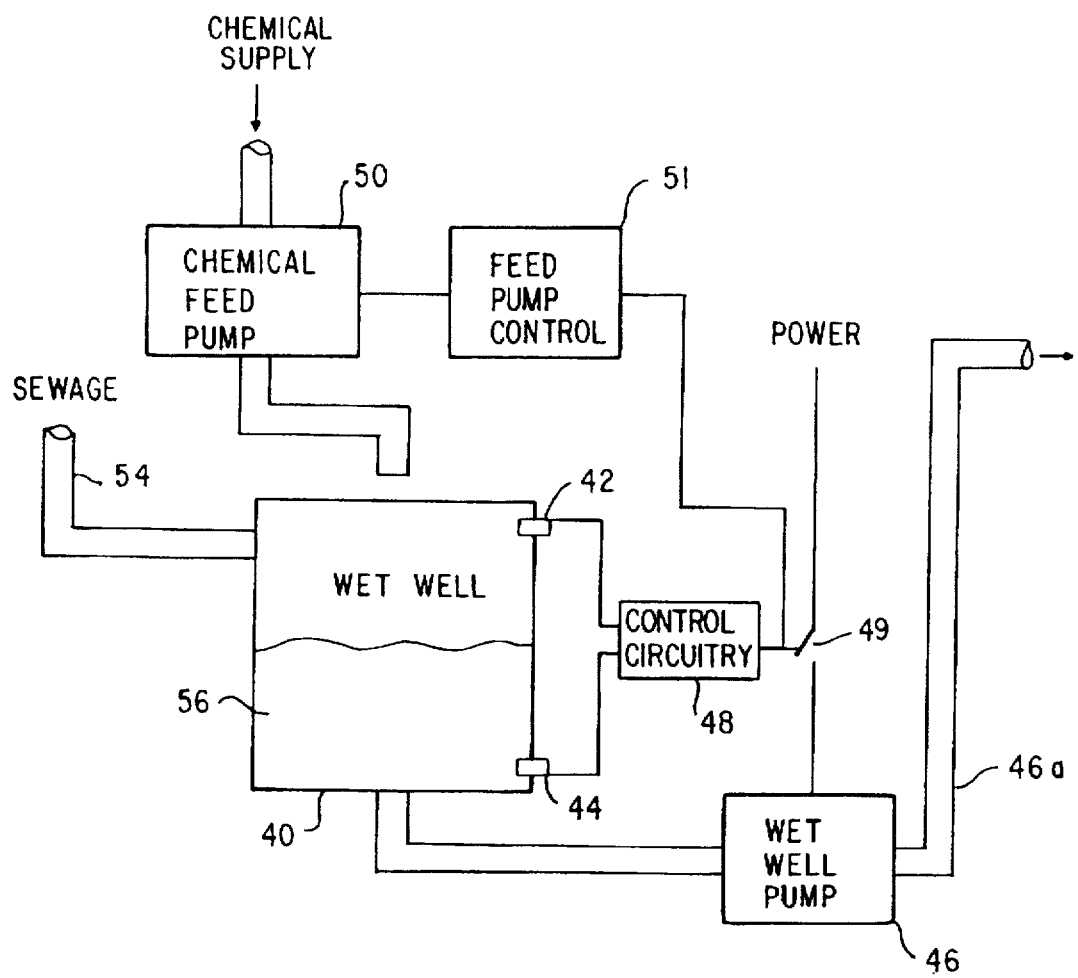
FIG. 5 is a schematic diagram of one embodiment of the invention in which a predetermined amount of chemical agent can be released into a wet well or other storage vessel upon receiving a signal from a feed pump control.

Referring now to FIG. 5, a separate embodiment of the present invention relates to a system for automatic batch feeding of a predetermined amount of sewage treatment chemical into a sewage containment vessel, such as a wet well, when there is a predetermined amount of sewage in the vessel.

Typically, a wet well 40 is connected to a pump 46 which operates to evacuate the wet well 40 when a particular amount or level of sewage is deposited therein via a sewage line 54. More specifically, when sewage has filled the wet well 40 or is at some predetermined level therein, a first transducer 42 generates a signal that is provided to control circuitry 48 which closes switch 49, thereby providing power to the pump 46. The pump 46 then evacuates sewage from the wet well 40 to allow room for further sewage and to transfer the accumulated sewage via what are typically referred to as force mains or gravity mains 46a for further treatment or disposal. At a point when the wet well 40 is substantially evacuated, the pump is shut off so as to allow the wet well 40 to once again fill with sewage. More specifically, a second transducer 44 senses when the wet well 40 has been evacuated or there is a predetermined amount of sewage contained therein and generates a signal that is provided to the control circuitry 48. In response, the control circuitry 48 opens switch 49 to turn off the pump 46. The filling up and evacuation of a typical wet well often occurs at different rates depending upon the time of day. For example, a wet well in a housing subdivision may go through a fill up/evacuation cycle eight to ten times an hour during morning hours when a significant number of people are performing their morning ablutions, but only once during the mid-day when most of these people are away at work.

One aspect of the present invention relates to the treatment of a given amount of sewage 56 in the wet well 40 with a sufficient amount of chemical agent to adequately prevent the formation of undesired compounds, such as hydrogen sulfide. To do so, the volume of the wet well 40 is determined and a volume of chemical agent is calculated for treating such volume of sewage. Upon the evacuation of the wet well 40 and the cessation of sewage pumping therefrom, the signal used to open switch 49 is also conveyed to a feed pump control unit 51 which operates to trigger the chemical feed pump 50 to release a predetermined amount of chemical into the wet well 40 within a predetermined amount of time, typically less than one minute. As sewage 56 then accumulates in the wet well 40, it mixes and reacts with the added chemicals to prevent the production of undesired compounds and odors. The incoming sewage mixes with the added chemicals until the high level mark on the wet well is again reached and the pump 46 is again activated to evacuate the wet well 40. In such a manner, batch processing of sewage in the wet well 40 is accomplished that makes efficient use of the treatment chemical and prevents the formation of undesirable compounds that may pose a health hazard as well as possibly damaging the sewage system.

Figure 6:
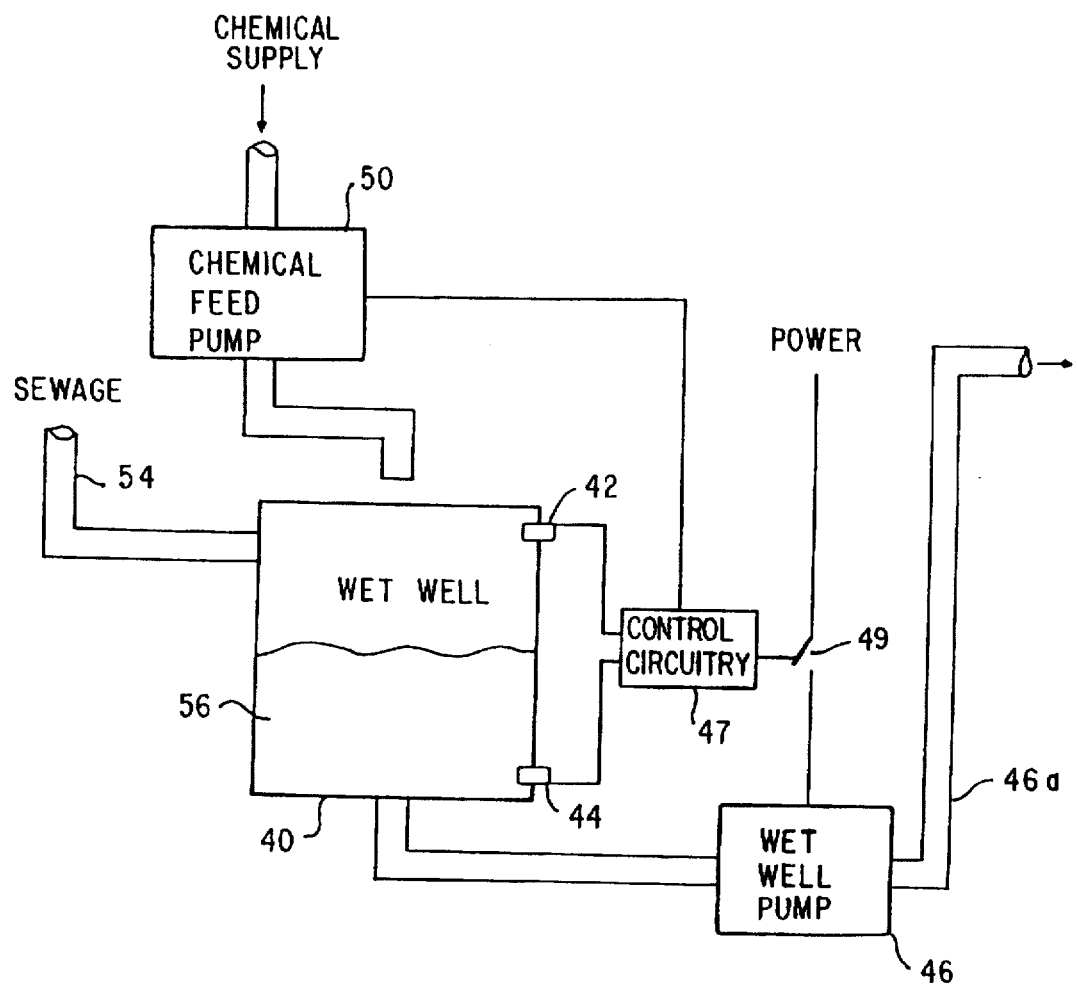
FIG. 6 is an alternate embodiment of the invention illustrated in FIG. 5.

To summarize the operation of the illustrated embodiment, the control circuitry 48 is activated by the first transducer 42 when the amount of sewage 56 reaches a certain high level point within the wet well 40. At such high sewage level the control circuitry 48 in turn sends a signal which activates the wet well pump 46 to evacuate the accumulated sewage 56. At a low level point when sewage 56 is substantially evacuated from the wet well 40 the control circuitry 48 is triggered by the second transducer 44 to shut off the pump 46. Upon a signal being transmitted to the control circuitry 48 by lower sensor 44 to cause cessation of pumping of sewage 56 from the wet well, and/or upon a signal being transmitted to the control circuitry 48 when the second transducer 44 is triggered by a low sewage level, the feed pump control 51 is activated to cause the chemical feed pump 50 to dose the wet well with an amount of chemical based upon the volumetric capacity of the evacuated wet well 46. The feed pump control 51 and the control circuitry 48 can be combined into one unit as illustrated in FIG. 6 and housed in lockable, corrosion resistant, weatherproof boxes fitted with mounting brackets for easy installation to wet well facilities. The present invention thus allows for the use of a compact, inexpensive chemical feed system which prevents the odor problems and corrosive problems encountered in conventional sewage treatment systems.

Alternative embodiments of the present invention include directly connecting the first and second transducers 42, 44 to a feed pump control that is adapted to process the signals provided by the transducers. Further, the chemical feed pump 50 can be triggered when the wet well 40 is partially filled with sewage, if so desired. Other embodiments include the programming of the control assembly 47 to trigger the evacuation of the wet well 40 and to discharge a predetermined amount of chemical into the wet well 40 at desired times of day or after predetermined sewage holding times. Automatic operation of the system may be achieved by installing into the various flow lines control items capable of monitoring and controlling various functions and cycles of the system. Hydraulic and atmospheric pressure switches may be used to control liquid levels and timer operated switches may be employed to achieve a self-sustaining continuous automatic operation.

The chemical agents used in the present invention are preferably able to complex with hydrogen sulfide or otherwise act to prevent bacterial generation of undesired compounds. The chemical deodorizing agents suitable for use in the present invention include, but are not limited to, chemical agents reactive with odorous compounds including those associated with fecal matter such as the indoles and skatoles, and sulfur containing compounds including mercaptans and sulfides, and particularly hydrogen sulfide. Preferably, the following chemical agents are used: Pond X2™ Odor Eliminator, Sulfaway $H_2S$ Scavenger and Sulf Control, Sulfide Inhibitor. Traditional metal salts, nitrates and oxidant chemical feed chemicals can also be utilized with the present invention.

Further, should it be desirable, the deodorizing invention illustrated in FIG. 1 can be used to treat odorous gases emanating from the sewage storage vessel or wet well or coming off of the forced line.

Figure 7B:
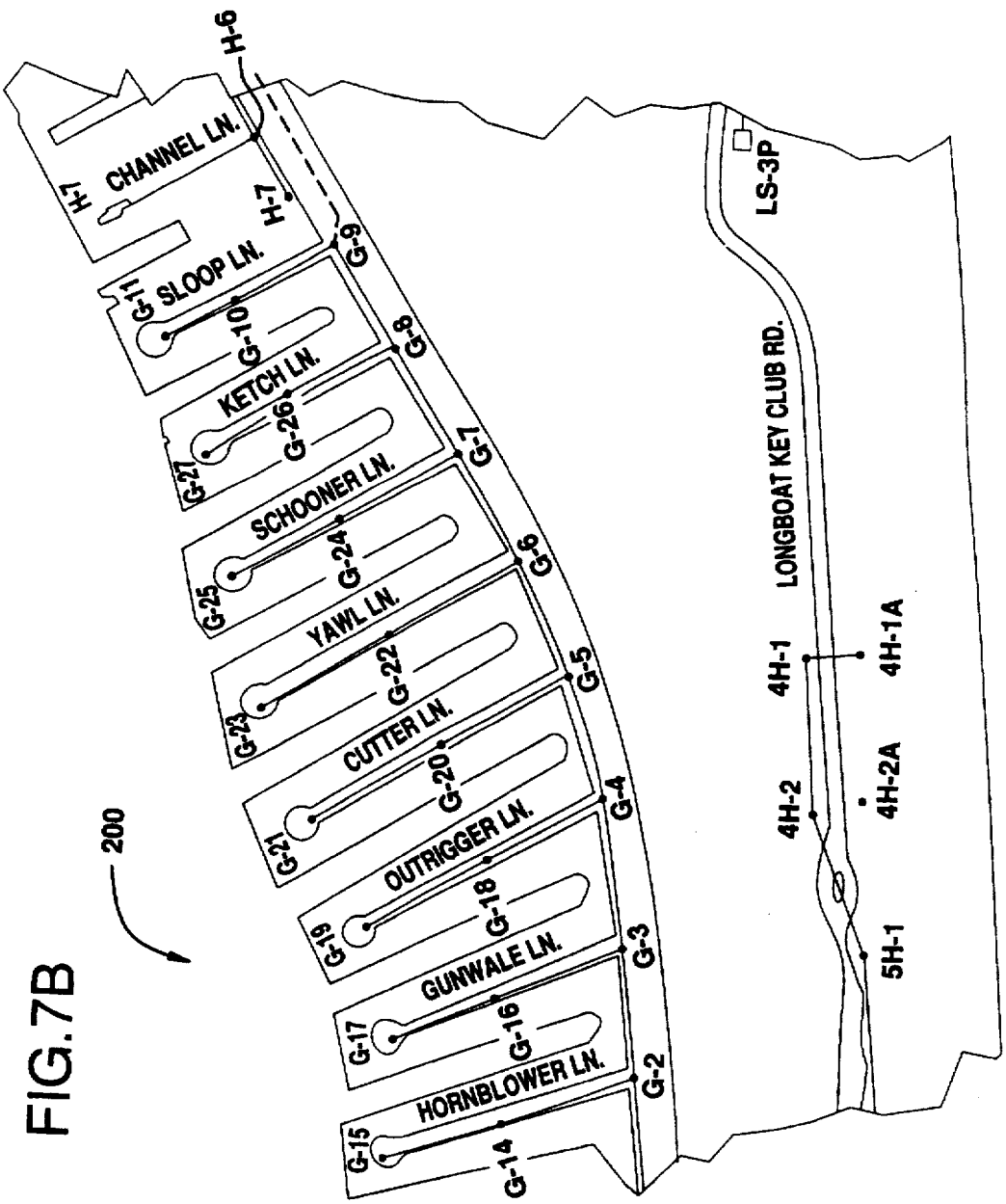
FIG. 7 is detailed diagram of a portion of the sewage collection system schematically illustrated in FIG. 7.

With reference to FIGS. 7–11, an apparatus and method that provides for the coordinated chemical treatment of a sewage collection system is discussed. FIG. 7 illustrates a portion of a sewage collection system 200 that is comprised of gravity mains 202, which are identified by solid lines and are fed by smaller gravity lines from homes and businesses adjacent thereto. Access to the gravity mains 202 is by manholes 204, which are identified by dark dots. The gravity mains 202 are so named because waste water or sewage flows in the mains due to gravity. When the topography no longer, allows the waste water to flow by gravity, a lift station 206 is employed to force the sewage through a force main 208 to a location where gravity will again move the sewage. The lift stations in FIG. 7 are identified by a small square and the force mains are identified by dashed lines. The sewage from two or more mains commingle at confluences 210 throughout the system 200. For example, the confluence 210 explicitly identified in FIG. 7 receives the sewage from lift station 2F, lift station 6F and lift station G, i.e. lift station 206.

FIG. 8 is a schematic diagram of all of the lift stations in the system 200. The main lift stations are designated by single capital letters and the smaller lift stations are identified by numerals preceding a letter. The force main from a main lift station is referred to as a main interceptor 212. The force mains that connect into a main interceptor are referred to as laterals 214. The entire waste water collection system 200 shown in FIG. 8 is designed to collect waste water throughout the system and transport it to a waste water treatment plant 216 for treatment.

A fundamental problem associated with sewage collection systems, such as the one illustrated in FIGS. 7 and 8, is the presence of sulfides. Specifically as sewage moves through the system 200, the oxidation reduction potential (ORP) of the sewage is reduced. Stated differently, the dissolved oxygen in the sewage diminishes. Eventually the dissolved oxygen diminishes to a point at which anaerobic bacteria can reduce the sulfates in the sewage to sulfides. The sulfides can then combine with hydrogen to form hydrogen sulfide $H_2S$, which presents odor, worker safety and corrosion problems.

Figure 9:
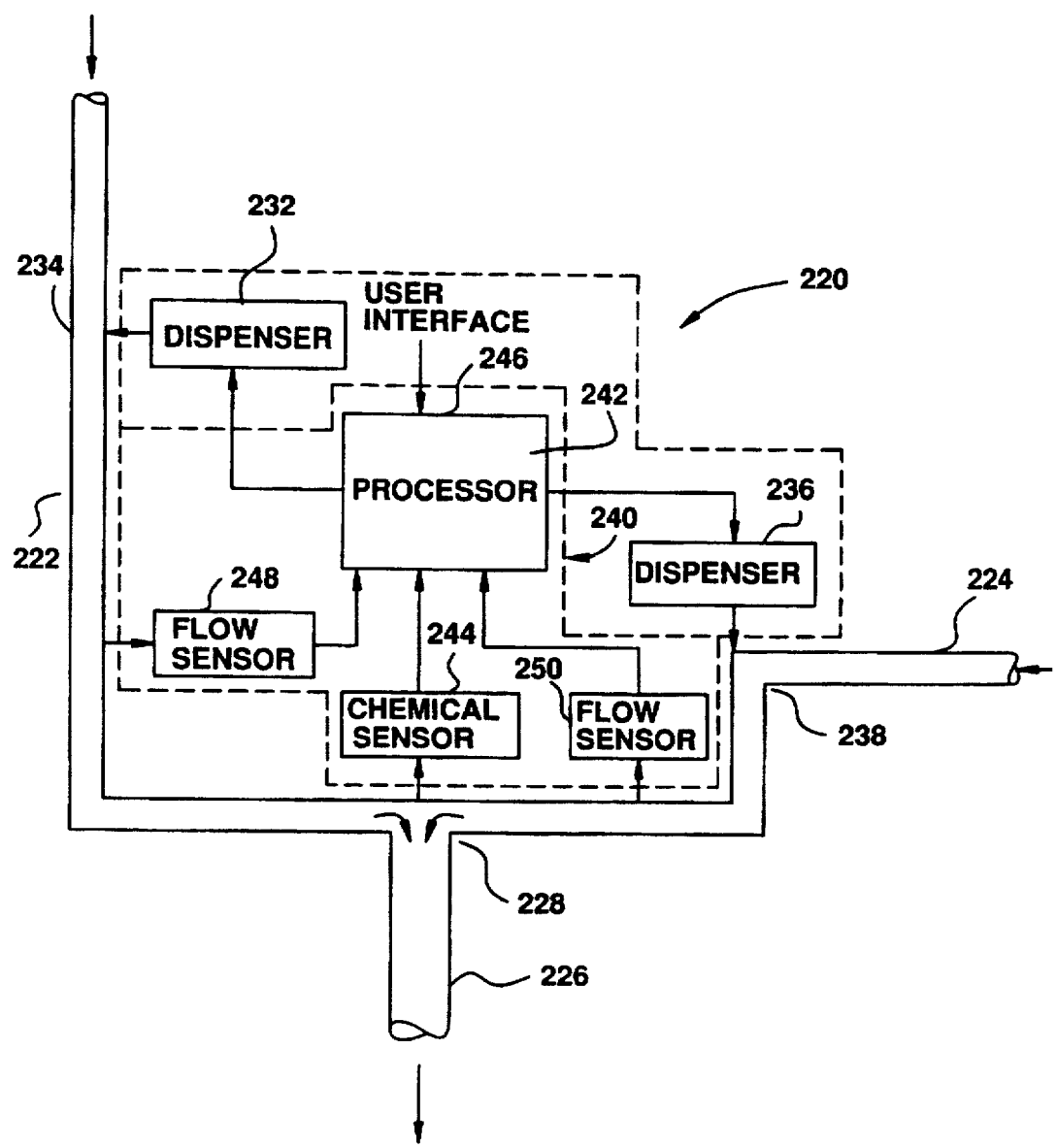
FIG. 9 illustrates the first embodiment of an apparatus for coordinating the dispensing of sewage treatment chemicals at two or more points in a sewage collection system.

With reference to FIG. 9, a coordinated chemical treatment apparatus 220, hereinafter referred to as apparatus 220, for chemically treating a sewage collection system to address the sulfide problem is discussed. As illustrated, the sewage collection system treated by the apparatus 220 is comprised of a first line 222, a second line 224 and a third line 226 that receives the sewage from the first line 222 and the second line 224 at a confluence 228. It should, however, be appreciated that the apparatus 220 can be extended to operate with a sewage collection system comprised of more than three lines and/or more than one confluence.

The apparatus 220 includes a first dispenser 232 for dispensing a sewage treatment chemical into the first line 222 at a first location 234; a second dispenser 236 for dispensing a sewage treatment chemical into the second line 224 at a second location 238; and a coordinator 240 for controlling the first dispenser 232 and the second dispenser 236 so that the chemical treatments in the first line 222 and the second line 224 reach the confluence 228 at substantially the same time and thereby facilitate treatment of sewage in the third line 226. It should be appreciated that the apparatus 220 can include more than two dispensers, each located to dispense a sewage treatment chemical at a different point in a sewage collection system.

Both the first and second dispensers 232, 236 operate in a batch mode. Specifically, in response to a signal from the coordinator 240, each of the dispensers injects an amount of sewage treatment chemical into a sewage line at a defined time and over a relatively short period of time. The amount of chemical injected into a line by a dispenser can be predetermined or defined in the signal provided by the coordinator. If necessary, a dispenser can dispense one or a combination of several sewage treatment chemicals. In this case, the signal from the coordinator can define which chemical or combination of chemicals is to be dispensed. The time at which a dispenser injects the sewage treatment chemical into the line can be immediately upon receiving the signal, after a predetermined delay, or after a delay defined within the signal from the coordinator 240.

The sewage treatment chemical provided by the dispensers is preferably anthraquinone, a pH modifier, or a combination thereof. Further, chemicals injected by the dispensers can be in a wet or dry form. In addition, the same or different sewage treatment chemicals can be injected into the lines with which each dispenser is associated to accommodate the characteristics of each of the lines.

The first and second dispensers 232, 236 can be either solar powered with a photovoltaic device, battery powered, pneumatically powered or connected to the municipal electricity grid. In addition, the first and second dispensers 232, 236 can communicate with the coordinator 240 via a hardwire system, pneumatic system, or a radio system.

The first and second dispensers 232, 236 are located at lift stations, manholes, or any other practical location in the collection system.

While the first and second dispensers 232, 236 have been described as operating in a batch mode, it is also possible that the first dispenser 232 and/or the second dispenser 236 can operate in a continuous mode, i.e., continually dispense a sewage treatment chemical into a line. In this case, the signal from the coordinator 240 is used to define the rate at which a dispenser operating in the continuous mode injects chemical into a line. Appropriate chemicals for continuous injection into a line are oxidizers, such as chlorine or hydrogen peroxide, bi-valent and tri-valent metal salts, such as ferrous sulfate ferric sulfate, ferrous chloride and ferric chloride, nitrates and pH modifiers, such as caustic soda.

The coordinator 240 includes a processor 242 that receives information on the sewage collection system and outputs, based upon this information, the appropriate signals to the first and second dispensers 232, 236 so that the chemical treatments applied to the first line 222 and the second line 224 reach the confluence 228 at substantially the same time and treatment of the third line 226 is achieved.

To provide the processor 242 with information, the coordinator 240 includes a chemical sensor 244 that, as illustrated, is located at the confluence 228 and informs the processor 242 when an undesirable level of a sewage related chemical parameter is present at the confluence 228. It should be appreciated that the chemical sensor 244 can, if necessary, be located at points other than a confluence and more than one chemical sensor can be employed. The chemical sensor 244 can sense sewage related chemical parameters such as total sulfides, dissolved sulfides, ambient $H_2S$, and the oxidation reduction potential (ORP) present in the sewage.

The coordinator 240 can also include a user interface 246 that permits other information, such as the length of the lines, the diameter of the lines, and the flow rates in the lines, to be provided to the processor 242. In the illustrated case, the length of the first line 222 between the location 234 at which the sewage treatment chemical is dispensed into the first line 222 and the confluence 228 can be measured and provided to the processor 242 via the interface 246. Likewise, the length of the second line 224 between the second location 238 at which the second dispenser 236 injects the sewage treatment chemical into the second line 224 and the confluence 228 can also be provided to the processor 242 via the user interface 246.

If the variance in the flow rate of one or more of the lines in a system is too great, the coordinator 240 can include one or more flow sensors to provide the processor 242 with flow rate information. In the illustrated embodiment, a first flow sensor 248 is provided to measure the flow rate of waste water in the first line 222 and provide this information to the processor 242, and a second flow sensor 250 is provided to measure the flow rate of waste water in the second line 224 and provide this information to the processor 242.

It should be appreciated at this point, that other information or different information than that previously discussed may be needed by the processor 242 to appropriately control the first and second dispensers 232, 236. In such a situation, if appropriate, measurements can be made and provided to the processor 242 via the user interface 24G or the appropriate sensors can be established in the apparatus. It should also be appreciated that the location, number, and type of sensors in the apparatus can be altered to accommodate the characteristics of each sewage collection system so long as at least one sensor provides feedback to the processor 242.

Operation of the apparatus 220 commences by characterizing the operation of the sewage collection system and providing the resulting information to the processor 242. Typically, the characterizing step involves measuring the length between dispensing and confluence points, measuring the flow rate related parameters for the lines in the system. and providing the information to the processor 242 via the user interface 246. Also, as part of the characterizing step, the chemical sensor 244 may detect an undesirable level of a sewage related parameter, such as ORP, and provide this information to the processor 242. In response, the processor 242 may further characterize the collection system by obtaining information from other sensors in the apparatus 220. For example, the processor 242 may request flow rate information from the first flow sensor 248 and/or the second flow sensor 250.

Based on the information provided by sensors or previously established in the processor 242, the processor 242 coordinates the dispensing of sewage treatment chemicals by the first dispenser 232 and the second dispenser 236 so that the residual sewage treatment chemicals from the first line 222 and the second line 224 reaches the confluence 228 at substantially the same time and can be used to treat the third sewage line 226. Specifically, the processor 242 provides a first signal to the first dispenser 232 that causes the first dispenser 232 to inject its sewage treatment chemical into the first line 222 at a first time. Similarly, the processor 242 provides a signal to the second dispenser 236 that causes the dispenser to inject its sewage treatment chemical into the second line 224 at a second time. The first and second times, based upon the available information, being chosen by the processor 242 so that the residual chemical treatment from each of the lines reaches the confluence at substantially the same time, and thereby chemically treats the third line 226.

Figure 10:
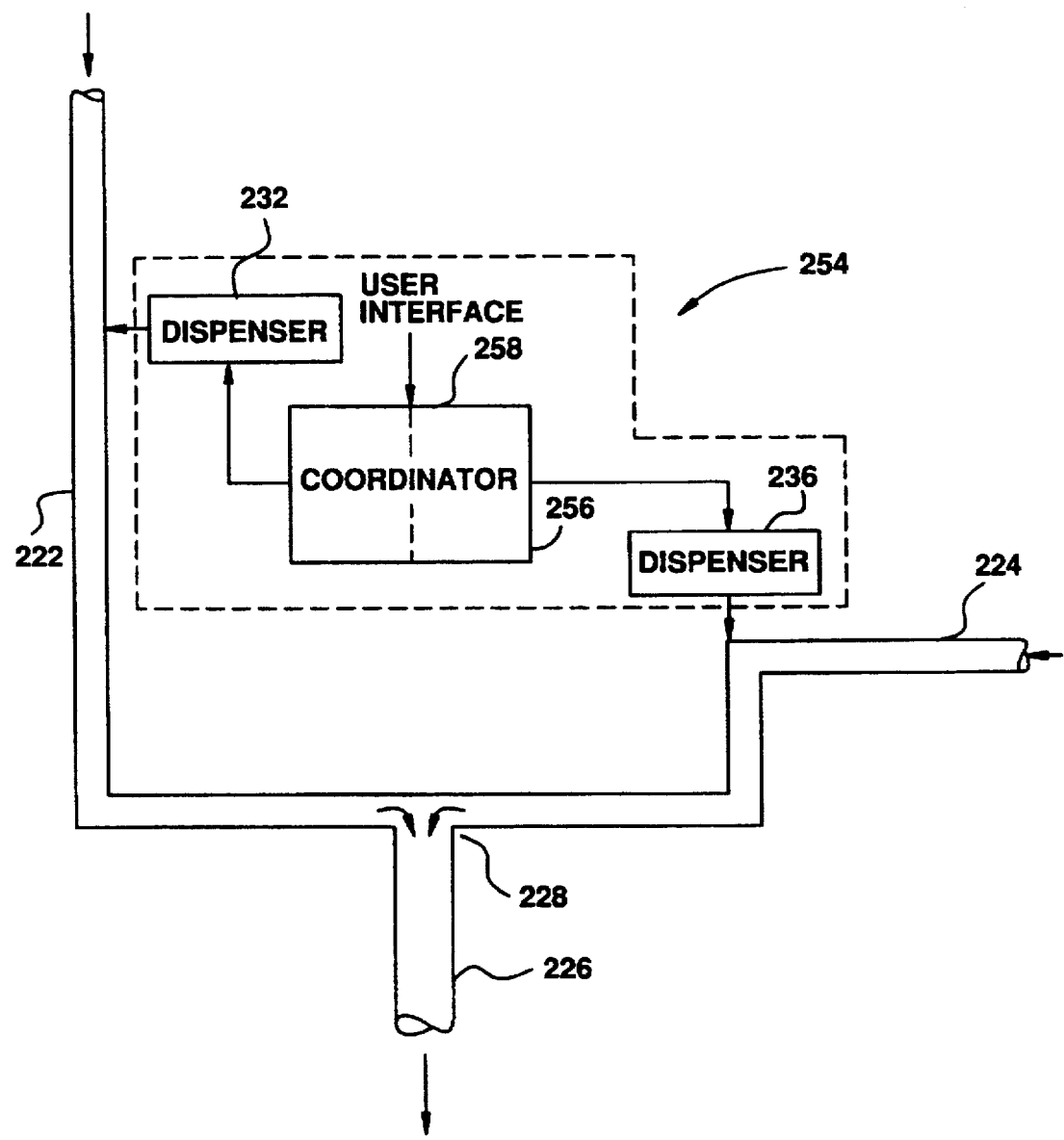
FIG. 10 illustrates a second embodiment of an apparatus for coordinating the dispensing of sewage treatment chemicals at two or more locations in a sewage collection system.

With reference to FIG. 10, a second embodiment of a coordinated chemical treatment apparatus 254, hereinafter referred to as apparatus 254, for chemically treating a sewage collection system is discussed. The sewage collection system treated by the apparatus 254 is identical to that treated by apparatus 220 and, as a consequence, has been given the same reference numbers as those shown in FIG. 9. Specifically, the sewage collection system treated by the apparatus 254 is comprised of a first line 222, a second line 224 and a third line 226 that receives the sewage from the first line 222 and the second line 224 at a confluence 228.

The portions of the apparatus 254 that correspond to those of the apparatus 220 have also been given the same reference numbers as those used with respect to apparatus 220. Specifically, the apparatus 254 includes a first dispenser 232 for dispensing a first sewage treatment chemical into the first line 222 at a first location 234 and a second dispenser 236 for dispensing a second sewage treatment chemical into the second line 224 at a second location 238.

In contrast to the apparatus 220, the apparatus 254 does not employ a chemical sensor or any other sensor for monitoring the sewage collection system. Rather, the apparatus 254 includes a coordinator 256 for causing, based upon the predetermined characteristics of the sewage collection system, the first dispenser 232 and the second dispenser 236 to inject their sewage treatment chemicals into the first line 222 and the second line 224, respectively, so that the residual sewage treatment chemicals reach the confluence 228 at substantially the same time and thereby result in treatment of the third line 226. The coordinator 256 can include a user interface 258 for inputting information to the coordinator 256 so that the coordinator can appropriately signal the first and second dispensers 232, 236. In one form, the coordinator 256 is a processor that has been programmed to generate the signals applied to the first and second dispensers 232, 236 at predetermined times. For example, the coordinator 256 may generate the signal applied to the first dispenser every four weeks and the signal applied to the second dispenser 236 every three weeks. Alternatively, the coordinator 256 can be realized by associating separate timers with the dispensers 232 and 236 and defining the times at which each of the timers causes a sewage treatment chemical to be dispensed to achieve the coordinated treatment of the system.

Operation of the apparatus 254 commences by characterizing the sewage collection system and using this information to program the coordinator 256. This information can be hardwired into the coordinator 256 or, if appropriate, entered by the user interface 258. Alternatively, the information can be used to program or define the injection times for separate timers associated with the first and second dispensers 232, 236. In any event, once the appropriate timing information has been provided to the coordinator 256, injection of sewage treatment chemicals by the first and second dispensers 232, 236 can commence. Typically, the operational parameters of the sewage collection system will be occasionally updated and, if necessary, the coordinator 256 adjusted.

Figure 11:
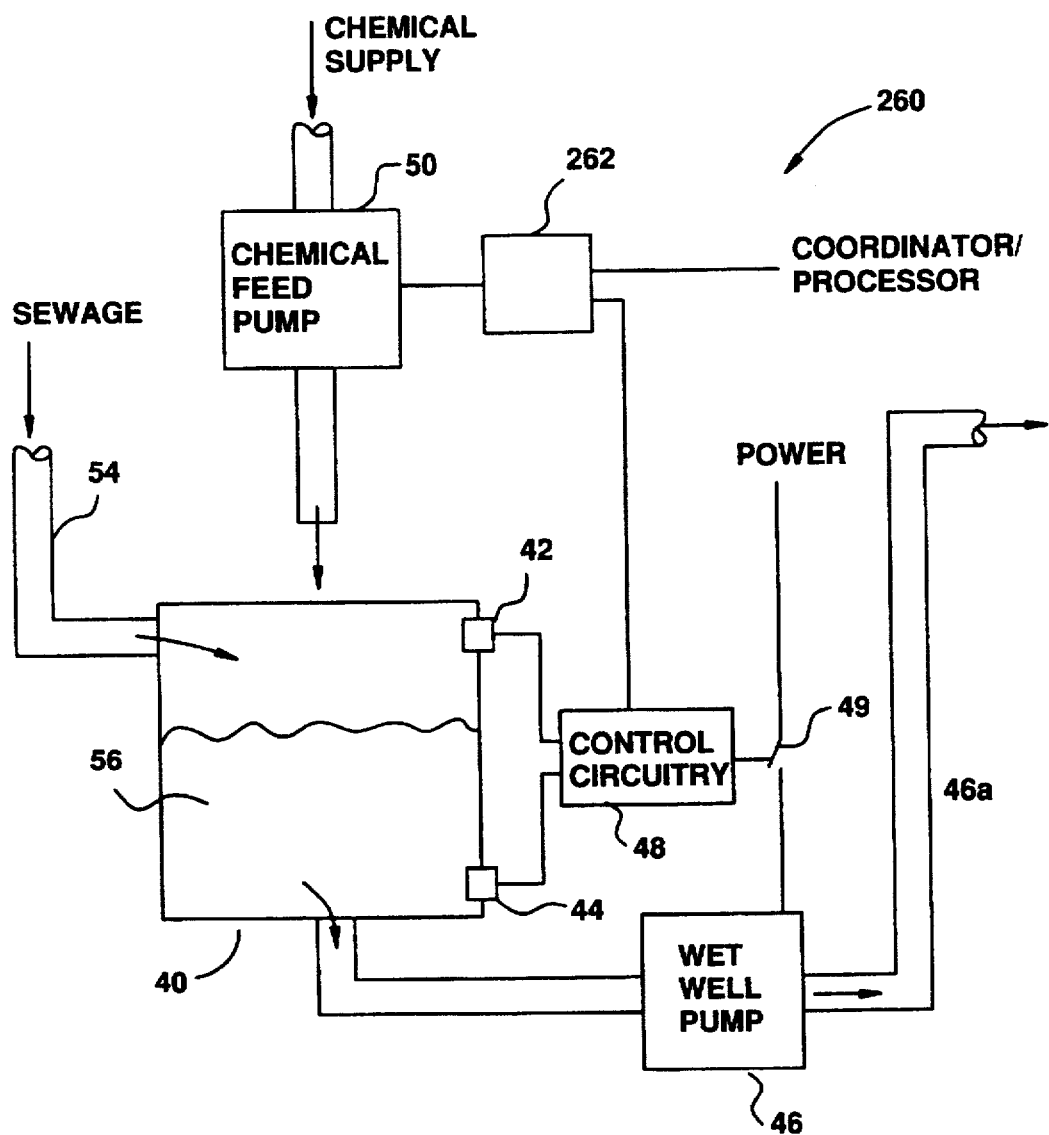
FIG. 11 illustrates a dispenser for dispensing a sewage treatment chemical into a wet well that can be used in the apparatuses illustrated in FIGS. 9 and 10.

FIG. 11 illustrates a dispenser 260 for injecting a sewage treatment chemical into a wet well in apparatus 220 or 254. The wet well is substantially identical to that shown in FIG. 6 and, as a consequence, the same reference numbers have been used to describe the wet well. In addition, the dispenser 260 employs much of the same circuitry associated with the dispenser illustrated in FIG. 5. Specifically, the dispenser 260 includes a first transducer 42, a second transducer 44, control circuitry 48, switch 49, and chemical feed pump 50. The operation of these elements has previously been described with respect to FIG. 6 and as a consequence, will not be described again. The dispenser 260, however, includes an additional element from that shown in FIG. 6. Specifically, the dispenser 260 includes dispenser circuitry 262 that causes a batch of sewage treatment chemical to be injected into the wet well upon receiving a signal from the control circuitry 48 indicating that the wet well is empty or has been filled to some other predetermined level and after having received a signal from the processor 242, associated with the apparatus 220 illustrated in FIG. 9, or coordinator 256, associated with the apparatus 254 illustrated in FIG. 10.

In operation, the dispenser 260, upon receiving a signal from the control circuitry 48 indicating that the wet well 40 is empty or has been filled to some other predetermined level and a signal from either the processor 242 or coordinator 256, causes the appropriate amount of sewage treatment chemical to be dispensed into the wet well 40. Consequently, the benefits associated with the dispenser illustrated in FIG. 6 as well as the benefits of coordinated treatment of the sewage collection system are realized. However, there may be some degradation in the aforementioned benefits, if the signal from the control circuitry 48 and the signal from the processor 242 or coordinator 256 are not present at substantially the same time. However, in sewage collection systems and specifically in sewage collection systems in which the wet wells fill rapidly, there is relatively little degradation in overall benefits.

While various embodiments of the present invention have been described in detail, it is apparent that modifications and adaptions of those embodiments will occur to those skilled in the art. It is to be expressly understood, however, that such modifications and adaption are within the scope of the present invention, as set forth in the following claims.

What is claimed is:

1. A sewage collection and treatment system, comprising:

a sewage treatment plant for separating the water from the solids in sewage;

a sewage collection system for receiving sewage from a plurality of sewage generating sites and transporting the received sewage to said sewage treatment plant, wherein the sewage in said sewage collection system flows in a downstream direction from each of said plurality of sewage generating sites to said sewage treatment plant, wherein said sewage collection system includes a first line for transporting a first sewage stream, a second line for transporting a second sewage stream that is separate from said first line, wherein said first line and said second line intersect and terminate at a commingling point that is the beginning of a third line for transporting both said first sewage stream and said second sewage stream towards said sewage treatment plant;

wherein said first line, said second line and said third line each may have sulfide related chemicals that are undesirable;

first means for dispensing a first batch of a first sewage treatment chemical into the sewage collection system at a first location on said first line of the sewage collection system over a first discrete period of time to treat sulfide related chemicals in said first line;

second means for dispensing a second batch of a second sewage treatment chemical into the sewage collection system at a second location on said second line in the sewage collection system over a second discrete period of time to treat sulfide related chemicals in said second line; and means for coordinating said first means for dispensing with said second means for dispensing so that any first unused portion of said first treatment chemical of said first batch and any second unused portion of said second treatment chemical of said second batch reach said commingling point at approximately the same time and thereby reduce the sulfide treatment requirements in said third line in the sewage collection system;

wherein said means for coordinating includes timer means for using information related to the times needed for said first and second sewage treatment chemicals to flow from said first and second locations, respectively, to said commingling point.

2. An apparatus, as claimed in claim 1, wherein:

at least one of said first means for dispensing and said second means for dispensing includes means for intermittently dispensing batches of a sewage treatment chemical into the sewage collection system.

3. An apparatus, as claimed in claim 1, wherein:

at least one of said first means for dispensing and said second means for dispensing includes one of the following: a battery, a photovoltaic device, a municipal electricity interface, and a pneumatic interface for providing power to the remainder of said at least one of said first means for dispensing and said second means for dispensing.

4. An apparatus, as claimed in claim 1, wherein:

at least one of said first means for dispensing and said second means for dispensing includes means for dispensing one of the following: anthraquinone, a pH modifier, and a combination of anthraquinone and a pH modifier.

5. An apparatus, as claimed in claim 1, wherein:

at least one of said first means for dispensing and said second means for dispensing includes means for dispensing one of the following: a liquid sewage treatment chemical and a solid sewage treatment chemical.

6. An apparatus, as claimed in claim 1, wherein:

said second treatment chemical is the same as said first sewage treatment chemical.

7. An apparatus, as claimed in claim 1, wherein:

said means for coordinating includes a chemical sensor for sensing a sewage related chemical parameters in one of said first line, said second line, and said third line.

8. An apparatus, as claimed in claim 1, wherein:

said timer means includes means for causing, in use, one of said first means for dispensing and said, second means for dispensing to dispense a sewage treatment chemical at a predetermined time.

9. An apparatus, as claimed in claim 1, wherein:

said timer means includes means for causing in use said first means for dispensing to dispense said first batch of said first sewage treatment chemical at a first predetermined time and said second means for dispensing to dispense said second batch of said second sewage treatment chemical at a second predetermined time;

wherein said first predetermined time is based upon the distance between said first location and said commingling point and the flow rate between said first location and said commingling point;

wherein said second predetermined time is based upon the distance between said second location and said commingling point and the flow rate between said second location and said commingling point;

wherein said first and second predetermined times are also based on the need for said first and second unused portions to reach said commingling point at approximately the same time.

10. An apparatus, as claimed in claim 9, wherein:

said means for coordinating includes means for sensing at least one of the following: a first rate of sewage flow between said first location and said commingling point so that said first predetermined time can be adjusted and a second rate of sewage flow between said second location and said commingling point so that said second predetermined time can be adjusted.

11. An apparatus, as claimed in claim 1, wherein:

said means for coordinating includes means for sensing a sewage related chemical parameter in at least one of said first, second and third lines and, after said sewage related parameter exceeds a predetermined threshold, providing a signal to said timer means;

wherein said timer means, in response to said signal, causes said first means for dispensing to dispense said first batch of said first sewage treatment chemical at a first predetermined time and said second means for dispensing to dispense said second batch of said second sewage treatment chemical at a second predetermined time;

wherein said first predetermined time is based upon the distance between said first location and said commingling point and the flow rate between said first location and said commingling point;

wherein said second predetermined time is based upon the distance between said second location and said commingling point and the flow rate between said second location and said commingling point;

wherein said first and second predetermined times are also based on the need for said first and second unused portions to reach said commingling point at approximately the same time.

12. An apparatus, as claimed in claim 11 wherein:

said means for coordinating includes means for sensing at least one of the following: a first rate of sewage flow between said first location and said commingling point so that said first predetermined time can be adjusted and a second rate of sewage flow between said second location and said commingling point so that said second predetermined time can be adjusted.

13. An apparatus, as claimed in claim 1, wherein:

said means for coordinating includes means for sensing one of the following sewage related parameters in one of said first line, said second line, and said third line: total sulfides, dissolved sulfides, ambient $H_2S$, and oxidation reduction potential.

14. An apparatus, as claimed in claim 1, wherein:

one of said first location and said second location includes a wet well; and said first means for dispensing or said second means for dispensing, whichever is located at said wet well, dispenses chemical upon receiving a first signal from said means for coordinating indicating that it is time to dispense chemical and a second signal indicating that said wet well is filled to a predetermined level.

15. An apparatus, as claimed in claim 1, further comprising:

additional means for dispensing at additional locations in the sewage collection system.

16. An apparatus, as claimed in claim 1, wherein:

said information includes a first distance between said first and third locations, a first rate of sewage flow between said first and third locations, a second distance between said second and third locations, and a second rate of sewage flow between said second and third locations.

17. An apparatus, as claimed in claim 1, wherein:

said means for coordinating includes means for sensing a rate for sewage flow between at least one of the following: said first location and said commingling point and said second location and said commingling point.

18. An apparatus, as claimed in claim 1, wherein:

said means for coordinating includes means for causing said first means for dispensing to dispense said first sewage treatment chemical at said first location and said second means for dispensing to dispense said second sewage treatment chemical at said second location at times so that said first sewage treatment chemical and said second sewage treatment chemical reach said third location at substantially the same time.

19. An apparatus for treating a sewage collection system that transports sewage from a plurality of sewage generating sites to a sewage treatment plant, wherein the sewage collection system includes a first line for transporting a first sewage stream, a second line for transporting a second sewage stream and that is separate from said first line, wherein said first line and said second line intersect and terminate at a commingling point that is the beginning of a third line for transporting both said first sewage stream and said second sewage stream towards the sewage treatment plant, wherein said first line, said second line and said third line each may have sulfide related chemicals that are undesirable, said apparatus comprising:

first means for dispensing a first batch of a first sewage treatment chemical at a first location on the first line in a sewage collection system over a first discrete period of time to treat sulfide related chemicals in the first line;

second means for dispensing a second batch of a second sewage treatment chemical at a second location on the second line in said sewage collection system over a second discrete period of time to treat sulfide related chemicals in the second line; and means for coordinating said first means for dispensing with said second means for dispensing so that any first unused portion of said first treatment chemical of said first batch and any second unused portion of said second treatment chemical of said second batch reach said commingling point at approximately the same time and thereby reduce the chemical treatment requirements downstream from the intersection point in the sewage collection system;

wherein said means for coordinating includes timer means for using information related to a first time needed for said first sewage treatment chemical to flow from said first location to said third location and a second time needed for said second sewage treatment chemical to flow from said second location to said third location.

20. An apparatus, as claimed in claim 19, wherein:

said timer means includes means for causing, in use, said first means for dispensing to dispense said first batch of said first sewage treatment chemical at a first predetermined time and said second means for dispensing to dispense said second batch of said second sewage treatment chemical at a second predetermined time;

wherein said first predetermined time is based upon the distance between said first location and said commingling point and the flow rate between said first location and said commingling point;

wherein said second predetermined time is based upon the distance between said second location and said commingling point and the flow rate between said second location and said commingling point;

wherein said first and second predetermined times are also based on the need for said first and second unused portions to reach said commingling point at approximately the same time.

21. An apparatus, as claimed in claim 20, wherein:

said means for coordinating includes means for sensing at least one of the following: a first rate of sewage flow between said first location and said commingling point so that said first predetermined time can be adjusted and a second rate of sewage flow between said second location and said commingling point so that said second predetermined time can be adjusted.

22. An apparatus, as claimed in claim 19, wherein:

said means for coordinating includes means for sensing a sewage related chemical parameter in at least one of said first, second and third lines and, after said sewage related parameter exceeds a predetermined threshold, providing a signal to said timer means;

wherein said timer means, in response to said signal, causes said first means for dispensing to dispense said first batch of said first sewage treatment chemical at a first predetermined time and said second means for dispensing to dispense said second batch of said second sewage treatment chemical at a second predetermined time;

wherein said first predetermined time is based upon the distance between said first location and said commingling point and the flow rate between said first location and said commingling point;

wherein said second predetermined time is based upon the distance between said second location and said commingling point and the flow rate between said second location and said commingling point;

wherein said first and second predetermined times are also based on the need for said first and second unused portions to reach said commingling point at approximately the same time.

23. An apparatus, as claimed in claim 22, wherein:

said means for coordinating includes means for sensing at least one of the following: a first rate of sewage flow between said first location and said commingling point so that said first predetermined time can be adjusted and a second rate of sewage flow between said second location and said commingling point so that said second predetermined time can be adjusted.

24. An apparatus, as claimed in claim 19, wherein:

said means for coordinating includes a chemical sensor for sensing a sewage related chemical parameter in one of said first line, said second line, and said third line.

25. An apparatus, as claimed in claim 19, wherein:

said means for coordinating includes means for sensing at least one of the following: a rate of sewage flow between said first location and said commingling point and a rate of sewage flow between said second location and said commingling point.

\* \* \* \* \*